US006740773B2

(12) United States Patent
Bohnen et al.

(10) Patent No.: US 6,740,773 B2
(45) Date of Patent: May 25, 2004

(54) PROCESS FOR PREPARING CYCLOHEXANEDICARBOXYLIC ESTERS

(75) Inventors: Hans Bohnen, Moers (DE); Thomas Klein, Oberhausen (DE); Klaus Bergrath, Oberhausen (DE)

(73) Assignee: Celanese Chemicals Europe GmbH (DE)

( * ) Notice: Subject to any disclaimer, the term of this patent is extended or adjusted under 35 U.S.C. 154(b) by 68 days.

(21) Appl. No.: 10/160,780

(22) Filed: Jun. 3, 2002

(65) Prior Publication Data

US 2003/0009051 A1 Jan. 9, 2003

(30) Foreign Application Priority Data

Jun. 16, 2001 (DE) ........................................ 101 29 129

(51) Int. Cl.[7] ................................................ C07C 69/74
(52) U.S. Cl. ...................................................... 560/127
(58) Field of Search ......................................... 560/127

(56) References Cited

U.S. PATENT DOCUMENTS 2,070,770 A * 2/1937 Amend

* cited by examiner

*Primary Examiner*—Paul J. Killos
(74) *Attorney, Agent, or Firm*—Muserlian, Lucas and Mercanti

(57) ABSTRACT

The invention relates to a process for preparing cyclohexanedicarboxylic esters (hexahydrophthalic diesters) by esterifying the corresponding benzenedicarboxylic acids and immediately hydrogenating the esterification mixture in the presence of nickel catalysts.

16 Claims, No Drawings

PROCESS FOR PREPARING CYCLOHEXANEDICARBOXYLIC ESTERS

The present invention relates to a process for preparing cyclohexanedicarboxylic esters (hexahydrophthalic diesters) by esterifying benzenedicarboxylic acids or anhydrides of these with linear or branched aliphatic $C_4$–$C_{14}$ monoalcohols, and then hydrogenating. The reaction of the aromatic dicarboxylic esters with hydrogen takes place in the presence of selected nickel catalysts in the gas or liquid phase.

STATE OF THE ART

Hydrogenated benzenedicarboxylic esters are used, inter alia, as intermediates in industrial organic chemistry and as plasticizers for plastics, for coating compositions, for sealing compounds, and in rubber products.

The effectiveness of the plasticizers derives from changes which they bring about in the physical properties of the highly polymerized thermoplastics, preferably using their solvating and swelling capability, but without reacting with the thermoplastics. Thermoplastic and plasticizer form a homogeneous system with a thermoplastic range shifted to lower temperatures than for the original polymer, the result being that the moldability and the elasticity of the polymer, for example, are increased and its hardness is reduced.

If plasticizers are to have a wide range of possible applications, they have to comply with a number of requirements. Ideally, they should be odorless, colorless, lightfast, low-temperature-resistant, and heat-resistant. In addition they are expected to undergo no change when exposed to moisture or water, and to be flame-retardant and have low volatility and, in particular, also to be toxicologically nonhazardous. In addition, their production should be simple and, in order to comply with environmental demands, avoid any formation of pollutant wastes, such as aqueous effluents comprising non-recyclable by-products and hazardous materials.

The compounds very widely used industrially as plasticizers include the esters of the isomeric phthalic acids, in particular esters which derive from ortho-phthalic acid and from plasticizer alcohols, i.e. linear or branched primary alcohols having from 4 to 14 carbon atoms in the molecule. They are used as single compounds or as mixtures of various esters. However, a factor which militates against their unrestricted use is that concerns have recently been raised as to whether this class of substances may be hazardous to health. They are therefore not permitted for use with food or drink, e.g. as a packaging material, or in other products whose use is subject to particular precautions for preventative healthcare reasons. Products of this type include, for example, items in day-to-day use, such as household articles and articles for childcare uses, including toys, and also products used in the medical sector. The plasticizers used for auxiliary or finished products made from thermoplastics and destined for these specific application sectors are not therefore phthalates, but compounds free from any toxic hazard. They include the esters of citric acid, whose application is limited for economic reasons to specific sectors, e.g. toys. Esters of cyclohexane di- and polycarboxylic acids (hexahydrobenzenedi- and -polycarboxylic acids) are much more freely available and therefore have potential for wider use.

The use of a cyclohexanedicarboxylic ester, namely 2-ethylhexyl cyclohexane-1,2-dicarboxylate, as plasticizer is known from DE-A 12 63 296. DE 199 27 977 A1 gives a comprehensive review of cyclohexanedi-, -tri-, and -tetracarboxylic esters which are suitable plasticizers for plastics. That publication in particular points out the advantageous toxicological properties of the compounds mentioned.

Cyclohexanedicarboxylic esters are usually prepared by catalytic hydrogenation of benzenecarboxylic esters. An example of a process of this type is the subject matter of DE 28 23 165 A1. The catalysts used in that procedure are in particular nickel but also the platinum metals ruthenium, rhodium or palladium, applied to a lithium aluminum spinel ($LiAl_5O_6$) support.

Another process for preparing cyclohexanedicarboxylic esters is described in DE 197 56 913 A1. In that publication, benzenedicarboxylic esters in the form of a single compound or in a mixture with other benzenedicarboxylic esters are reacted with a gas comprising hydrogen in the presence of a catalyst which encompasses at least one metal of the 8th transition group of the Periodic Table, alone or together with at least one metal of the 1st or 7th transition group of the Periodic Table, applied to a support which has macropores. Ruthenium in particular is used as catalytically active metal.

The known processes require the use of pure benzenedicarboxylic esters. The starting compounds therefore have to be subjected to complicated purification steps after their synthesis and prior to the reaction with hydrogen. The processes of the prior art also rely on the use of platinum metal catalysts, in particular ruthenium catalysts, for carrying out the hydrogenation. Reclamation of the catalysts has to be as quantitative as possible in order to restrict losses of precious metal over the entire reaction. The methods required for this purpose necessitate further steps in the reaction and therefore the provision of additional sections of plant. In these circumstances it is of interest to simplify the preparation process and to use appropriate conduct of the reaction to restrict the number of steps in the reaction to a minimum and thus increase the cost-effectiveness of the process.

OBJECTS OF THE INVENTION

It is an object of the present invention to provide a process which prepares cycloaliphatic dicarboxylic esters from the corresponding benzenedicarboxylic acids or anhydrides of these and which links the benzenedicarboxylic ester synthesis with the subsequent hydrogenation to give an integral process in such a way that separate steps for isolation and purification can be dispensed with.

THE INVENTION

According to the invention, the object described above is achieved by means of a process for preparing cyclohexanedicarboxylic esters by esteryfing of a benzenedicarboxylic acid or a benzenedicarboxylic anhydride with an aliphatic $C_4$–$C_{14}$ monoalcohol in the presence of an acid or of a catalyst containing titanium, zirconium or tin, at temperatures of from 100 to 250° C., with removal of any water formed and neutralization of the reaction mixture once the esterification has been completed by adding an alkaline reagent, which comprises hydrogenating the neutralized esterification mixture where appropriate after removal of the water generated by the neutralization without other pretreatment in the presence of a nickel catalyst, and then isolating the cyclohexanedicarboxylic ester by separating off the by-products from the reaction mixture.

The novel process permits cyclohexanedicarboxylic esters to be prepared in successive steps of a reaction starting from benzenedicarboxylic acids or anhydrides of these. It should be particularly emphasized that isolation of intermediates is not necessary either for reasons of process technology or in connection with intermediate purification steps. Nevertheless, the products obtained from the reaction are highly pure esters of cycloaliphatic dicarboxylic acids and comply with all of the requirements which permit their successful use as plasticizers. In particular, the esters have excellent color properties, such as colorfastness, and extremely low conductivity, properties which give them a broad field of application in plastics processing.

The novel process starts from dicarboxylic acids or dicarboxylic anhydrides of benzene and from aliphatic monoalcohols having from 4 to 14 carbon atoms in the molecule as starting compounds. For the purposes of the invention, dicarboxylic acids of benzene are understood to be the positional isomers phthalic acid (o-phthalic acid), isophthalic acid (m-phthalic acid), and terephthalic acid (p-phthalic acid), in particular o-phthalic acid. The alcohol component of the esters may be either linear or branched compounds of the molecular size mentioned. Preference is given to alcohols having from 4 to 10 carbon atoms in the molecule, e.g. n-butanol, n-octan-1-ol, n-octan-2-ol, 2-ethylhexanol, n- and isononyl alcohols, n- and isodecyl alcohols and those known as oxo alcohols, i.e. mixtures of linear and branched alcohols of appropriate molecular size which are obtained from olefins via an oxo reaction and subsequent hydrogenation.

The esters are prepared in a known manner by reacting dicarboxylic acid or dicarboxylic anhydride with alcohol, which is frequently present in excess, in the presence of a catalyst. In the traditional processes the catalysts are acids, e.g. sulfuric acid. Modern processes use metal-containing esterification catalysts, in particular tin, titanium, and zirconium in the form of the finely divided metals, or as salts, oxides, or organic compounds soluble in the reaction mixture.

The reaction of the starting materials present in the mixture usually takes place at from 100 to 250° C., with stirring, in one stage or two or more stages characterized by different temperature ranges. Water produced in the reaction is advantageously removed as azeotrope, e.g. using cyclohexane or the alcohol used for the esterification as azeotrope components.

Once the reaction has been completed, the esterification mixture still comprises in particular excess alcohol and the catalyst, alongside the desired reaction product, the diester.

To neutralize the acidic constituents and to remove the catalyst, the reaction mixture is reacted with an alkaline reagent. Suitable alkaline compounds are alkali metal hydroxides or alkaline earth metal hydroxides, or alkali metal carbonates, used as an aqueous solution. The concentration of the alkaline compounds in the solution is usually from 5 to 20% by weight, based on the solution. The amount of the neutralization agent to be added depends on the proportion of acidic components in the crude product. This proportion is determined as the acid value (to DIN 53169). In the new process it is not necessary for the amount of the alkaline reagent added to the esterification mixture to be exactly equivalent to the $H^+$ ions present for neutralization. Instead, an excess of the alkaline reagent may be used, corresponding to up to ten times, and in one particularly preferred embodiment of the new procedure from two to four times, the amount stoichiometrically required to neutralize the $H^+$ ions.

Following the neutralization, the crude esterification mixture is reacted with hydrogen without further pretreatment. The only advisable measure is that water generated by the neutralization, if it is present as a separate phase, be removed in advance, advantageously by simply separating the organic and aqueous phases.

According to the invention, the hydrogenation is carried out in the presence of nickel catalysts. The catalytically active metal has been applied to a support, the amount generally being from about 5 to about 70% by weight, preferably from about 10 to about 65% by weight, and in particular from about 20 to about 60% by weight, based in each case on the total weight of the catalyst. Suitable catalyst supports are any of the conventional support materials, e.g. aluminum oxide, the various types of aluminum oxide hydrates which occur, silicon dioxide, polysilicic acids (silica gels) including kieselguhr, silica xerogels, magnesium oxide, zinc oxide, zirconium oxide, and activated carbon. Besides the main components nickel and support material, the catalysts may also comprise subordinate amounts of additives which serve, for example, to improve their hydrogenation activity and/or their operating time, and/or their selectivity. Additives of this type are known and include, for example, the oxides of sodium, of potassium, of magnesium, of calcium, of barium, of zinc, of aluminum, of zirconium, and of chromium. The total proportion of these added to the catalyst is generally from 0.1 to 50 parts by weight, based on 100 parts by weight of nickel.

The catalysts used in the process of the invention are prepared by conventional processes. For example, the active hydrogenation constituent nickel, and additives present where appropriate, may be precipitated together with the support from aqueous solutions which comprise an appropriate composition of the catalyst constituents dissolved in the form of salts. Another possible procedure starts from suspended support material onto which the component active in hydrogenation is precipitated, if desired together with additives. Finally, another way of obtaining suitable catalysts is saturation of support substances with solutions of the metal active in hydrogenation and of possible additives. The catalysts are usually used after molding, e.g. in the form of tablets or extrudates or grains.

According to the invention, the hydrogenation is carried out at temperatures of from about 50 to about 250° C., preferably from 80 to 220° C. The pressure used is generally 1 MPa or above, preferably from about 2 to 30 MPa.

The novel process is carried out batchwise or continuously in the liquid phase with suspended catalysts or in the liquid or gas phase with fixed catalysts; the continuous procedure is preferred.

In the case of batchwise conduct of the process the amount of nickel used in the form of the catalyst described above is from 1 to 10% by weight, preferably from 2 to 6% by weight, based on the starting ester or the ester mixture. In the case of a continuous procedure, the amount used of the starting ester or ester mixture per liter of catalyst and hour is from about 0.05 to about 5.0 kg, and preferably about 0.1 to 2.0 kg of ester is used per liter of catalyst and hour.

Pure hydrogen is preferably used for the hydrogenation. However, it is also possible to use mixtures which comprise free hydrogen and, alongside this, constituents inert under the conditions of the hydrogenation. In all cases, care has to be taken that the hydrogenation gas is free from detrimental amounts of catalyst poisons, such as sulfur compounds or carbon monoxide.

The ester or ester mixture starting material may be used as it stands or together with a solvent or diluent, the last-named variant being preferred. The selection of the solvents or diluents, which may be either pure substances or else mixtures of substances, is not critical as long as it is ensured that it forms a homogeneous solution with the starting material. Examples of suitable solvents or diluents are aliphatic alcohols having up to 10 carbon atoms in the molecule, in particular the $C_3$–$C_6$ alcohols, e.g. the isomeric propanols and butanols, and also n-hexanol and linear or cyclic ethers, such as tetrahydrofuran or dioxane. The amount used of the solvent or diluent may be freely selected as appropriate for the apparatus and process technology used, and use is generally made of solutions which comprise from 10 to 75% by weight of starting ester or starting ester mixture. For the purposes of the process of the invention, it has proven particularly successful to use the product produced during the hydrogenation as solvent or diluent. In that case, the amount of the hydrogenated product added as solvent or diluent is advantageously from 1 to 30 times, preferably from 5 to 20 times, and in particular from 5 to 10 times, the weight of the compound to be hydrogenated.

To obtain the pure cyclohexanedicarboxylic ester, the constituents with lower boiling points than the cyclohexanedicarboxylic ester are distilled out from the hydrogenation mixture. This distillation may take place either at atmospheric pressure or else at subatmospheric pressure. One distillation step is generally sufficient, but in exceptional cases only a second distillation stage may be required.

The process of the invention is described in more detail below using some examples, but is not limited to the embodiments described.

EXAMPLES

The esterification mixtures used as starting material in the following examples have been prepared by reacting phthalic anhydride with 2-ethylhexanol in the presence of sulfuric acid as catalyst and then neutralizing the reaction product.

The esterification mixture used in the hydrogenation had the following composition determined by gas chromatography (data in % by weight); DEHP is di(2-ethylhexyl) phthalate.

| | |
|---|---|
| Forerun | 0.89 |
| 2-Ethylhexanol | 11.34 |
| Intermediate fraction | 0.37 |
| DEHP | 87.40 |

The reaction with hydrogen was carried out in the liquid phase at a temperature of 140° C. and a pressure of 8 MPa. The hydrogenation time depended on the hydrogen absorption, and when this had been completed hydrogenation was continued for a further 30 min to complete the reaction, and this was followed by cooling, depressurization, and gas-chromatographic analysis on the hydrogenation mixture after the catalyst had been removed by filtration.

Examples 1–4

These examples used varying amounts of a catalyst comprising 55% by weight of nickel, 6% by weight of magnesium oxide and about 34% by weight of kieselguhr.

Example 1

2% by weight of catalyst, based on the esterification mixture used

| | |
|---|---|
| Forerun | 3.86 |
| 2-Ethylhexanol | 10.90 |
| Intermediate fraction | 0.68 |
| DEHP | 77.11 |
| Hydrogenated DEHP | 7.45 |

Example 2

3% by weight of catalyst, based on the esterification mixture used

| | |
|---|---|
| Forerun | 0.59 |
| 2-Ethylhexanol | 10.90 |
| Intermediate fraction | 0.74 |
| DEHP | 42.32 |
| Hydrogenated DEHP | 45.45 |

Example 3

4% by weight of catalyst, based on the esterification mixture used

| | |
|---|---|
| Forerun | 0.72 |
| 2-Ethylhexanol | 11.99 |
| Intermediate fraction | 0.41 |
| DEHP | 0.42 |
| Hydrogenated DEHP | 86.46 |

Example 4

5% by weight of catalyst, based on the esterification mixture used

| | |
|---|---|
| Forerun | 1.40 |
| 2-Ethylhexanol | 10.46 |
| Intermediate fraction | 0.52 |
| DEHP | 0.16 |
| Hydrogenated DEHP | 87.46 |

Examples 5 to 8

These examples used varying amounts of a catalyst comprising 60% by weight of nickel, about 27% by weight of kieselguhr and about 3% by weight of aluminum oxide.

Example 5

2% by weight of catalyst, based on the esterification mixture used

| | |
|---|---|
| Forerun | 0.74 |
| 2-Ethylhexanol | 11.98 |
| Intermediate fraction | 0.69 |

-continued

| | |
|---|---|
| DEHP | 48.78 |
| Hydrogenated DEHP | 37.81 |

Example 6

3% by weight of catalyst, based on the esterification mixture used

| | |
|---|---|
| Forerun | 0.36 |
| 2-Ethylhexanol | 10.02 |
| Intermediate fraction | 0.44 |
| DEHP | 0.39 |
| Hydrogenated DEHP | 88.79 |

Example 7

4% by weight of catalyst, based on the esterification mixture used

| | |
|---|---|
| Forerun | 0.73 |
| 2-Ethylhexanol | 11.47 |
| Intermediate fraction | 0.53 |
| DEHP | 0.43 |
| Hydrogenated DEHP | 86.84 |

Example 8

5% by weight of catalyst, based on the esterification mixture used

| | |
|---|---|
| Forerun | 0.10 |
| 2-Ethylhexanol | 7.76 |
| Intermediate fraction | 0.46 |
| DEHP | 0.12 |
| Hydrogenated DEHP | 91.56 |

The di(2-ethylhexyl) ester of the cyclohexane-1,2-dicarboxylic acid was isolated in plasticizer quality by using distillation at 120° C. and 0.01 MPa to remove those constituents of the hydrogenation mixture which have lower boiling points than the desired reaction product.

What is claimed is:

1. A process for preparing cyclohexanedicarboxylic esters comprising esterifying a benzenedicarboxylic acid or a benzenedicarboxylic acid anhydride with an aliphatic monoalcohol of 4 to 14 carbon atoms in the presence of an acid or of a member of the group consisting of titanium, zirconium and tin, at 100 to 250° C., with removal of any water formed, neutralization of the reaction mixture once the esterification has been completed by adding an alkaline reagent, hydrogenating the neutralized esterification mixture where appropriate after removal of the water generated by the neutralization without other pretreatment in the presence of a nickel catalyst, and isolating the cyclohexanedicarboxylic ester by separating off the by-products from the reaction mixture.

2. The process of claim 1, wherein the benzenedicarboxylic acid or the benzenedicarboxylic anhydride is o-phthalic acid or o-phthalic acid anhydride.

3. The process of claim 1 wherein the aliphatic alcohol is an alcohol of 4 to 10 carbon atoms.

4. The process of claim 1 wherein the amount of the alkaline reagent added to the esterification mixture is up to ten times the amount stoichiometrically required to neutralize the $H^+$ ions present.

5. The process of claim 4 wherein the amount of alkaline reagent is 2 to 4 times.

6. The process of claim 1 wherein the catalyst comprises, based on the total weight of the catalyst, from 5 to 70% by weight of nickel.

7. The process of claim 6 wherein the catalyst has 20 to 60% by weight of nickel.

8. The process of claim 1 wherein the hydrogenation is carried out at 50 to 250° C., and at pressures of at least 1 MPa.

9. The process of claim 1 wherein the hydrogenation takes place continuously in the liquid or gas phase.

10. The process of claim 9, wherein use is made, based on ester or ester mixture used, of from 1 to 10% by weight of nickel in the form of nickel catalyst, in the case of a batchwise procedure.

11. The process of claim 9 wherein, per liter of catalyst and hour, use is made of from 0.05 to 5.0 kg of ester or ester mixture, in the case of a continuous procedure.

12. The process of claim 1 wherein the ester or ester mixture used in the hydrogenation has been dissolved in a solvent or diluent.

13. The process of claim 12 wherein the solution comprises from 10 to 75% by weight of ester or ester mixture.

14. The process of claim 12 wherein the solvent of diluent is the product produced during hydrogenation of the ester or of the ester mixture.

15. The process of claim 14 wherein the amount of the hydrogenated product used as solvent or as diluent is from 1 to 30 times the weight of the ester or ester mixture to by hydrogenated.

16. The process of claim 15 wherein the amount of hydrogenated product is 5 to 10 times the weight of the ester or ester mixture.

* * * * *